(12) United States Patent
Meazza et al.

(10) Patent No.: US 9,676,726 B2
(45) Date of Patent: Jun. 13, 2017

(54) PROCESS FOR THE REGIOSELECTIVE SYNTHESIS OF PYRAZOLES

(71) Applicant: ISAGRO S.P.A., Milan (IT)

(72) Inventors: Giovanni Meazza, Saronno (IT); Laura Sillani, Borgomanero (IT); Pierangelo Mereghetti, Inveruno (IT); Daniele Forgia, Borgomanero (IT)

(73) Assignee: ISAGRO S.P.A., Milan (IT)

( * ) Notice: Subject to any disclaimer, the term of this patent is extended or adjusted under 35 U.S.C. 154(b) by 0 days.

(21) Appl. No.: 15/104,094

(22) PCT Filed: Dec. 23, 2014

(86) PCT No.: PCT/IB2014/067258
§ 371 (c)(1),
(2) Date: Jun. 13, 2016

(87) PCT Pub. No.: WO2015/097658
PCT Pub. Date: Jul. 2, 2015

(65) Prior Publication Data
US 2016/0318874 A1  Nov. 3, 2016

(30) Foreign Application Priority Data
Dec. 23, 2013  (IT) .............................. MI2013A2201

(51) Int. Cl.
C07D 231/14    (2006.01)
C07C 243/28    (2006.01)
(52) U.S. Cl.
CPC .......... *C07D 231/14* (2013.01); *C07C 243/28* (2013.01)
(58) Field of Classification Search
None
See application file for complete search history.

(56) References Cited

FOREIGN PATENT DOCUMENTS

WO  2012084812  6/2012

OTHER PUBLICATIONS

Raw et al., A one-pot process for the regioselective synthesis of 1,3,4-trisubstituted-1H-pyrazoles, Tetrahedron Letters, 50:696-699 (2009).

(Continued)

*Primary Examiner* — Kamal Saeed
(74) *Attorney, Agent, or Firm* — Florek & Endres PLLC

(57) ABSTRACT

A process is described for the synthesis of pyrazoles having general formula (I)

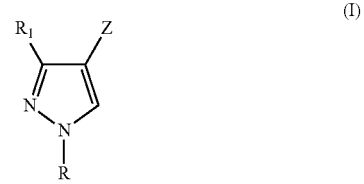

which comprises the steps of mixing a compound having general formula (II)

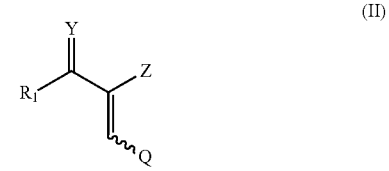

and a 1,2-disubstituted hydrazine having general formula (III)

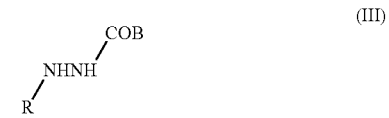

to form a reaction intermediate having general formula (IV)

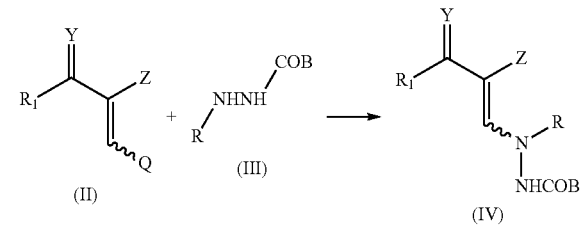

and the reaction mixture obtained in step i), in an acid environment, cyclizes to form a pyrazole having general formula (I), according to reaction scheme 1

Scheme 1

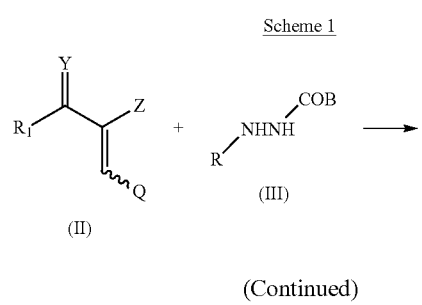

(Continued)

15 Claims, No Drawings

(56) References Cited

OTHER PUBLICATIONS

Menozzi et al., Reaction of 2-dimethylaminomethylene-1,3-diones with dinucleophiles. VI. Synthesis of ethyl or methyl 1,5-disubstituted 1H-pyrazole-4-carboxylates, Journal of Heterocyclic Chemistry, 24:1669-1675 (1987).
International Search Report and Written Opinion of the International Searching Authority in PCT/IB2014/067258 (Mar. 3, 2015).
Search Report and Written Opinion in Italian Application No. MI20132201 (Apr. 22, 2014).

PROCESS FOR THE REGIOSELECTIVE SYNTHESIS OF PYRAZOLES

The present invention relates to a new process for the regioselective synthesis of pyrazoles.

In particular, the present invention relates to a process for the regioselective synthesis of pyrazoles substituted by specific groups in positions 1, 3 and 4 of the heterocyclic ring.

1,3,4-substituted pyrazoles are used as intermediates in the pharmaceutical field, as described, for example, in Pharmaceuticals (2012), vol. 5, pages 317-324, WO 2004/4039365, US 2012/0122907, US 2013/0012715, US 2006/0079562, or in the agrochemical field, as described, for example, in U.S. Pat. No. 5,747,518, WO 93/11117, WO 2012/084812.

The use of derivatives of 1,3-disubstituted 4-pyra-zolcarboxylic acids has proved to be of particular applicative interest.

These compounds are normally prepared by the cyclization of suitable derivatives of acrylic acid with monosubstituted hydrazines, as indicated in the reaction scheme A:

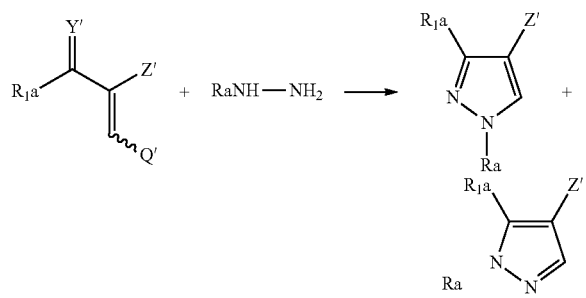

scheme A wherein Y' represents oxygen or sulphur, Q' represents an outgoing group, such as, for example, an alkoxyl and $R_a$, $R_{1a}$ and Z' represent the substituents in position 1, 3 and 4 of pyrazole.

As can be seen from the reaction scheme indicated above, the disadvantage of this method consists in the fact that significant quantities of 1,4,5-substituted pyrazole regioisomer are generally formed.

In addition to lowering the yields to the 1,3,4-substituted product, the lack of regioselectivity requires the separation of the two regioisomers, considerably increasing the production costs of the production process.

The Journal of Heterocyclic Chemistry (1987), vol. 24, pages 1669-1675, for example, describes the preparation of ethyl 1,3-dimethyl-1H-pyrazole-4-carboxylate together with the regioisomer ethyl 1,5-dimethyl-1H-pyrazole-4-carboxylate, by the reaction of ethyl 2-(dimethylaminomethylidene)-3-oxo-butanoate with methyl-hydrazine. The 1,3,4-substituted product is obtained with a regioselectivity of 23% and an overall yield to the two isomers of 88%, operating in methanol as solvent, with a regioselectivity of 76% and an overall yield to the two isomers of 77%, operating in diethyl ether.

The Australian Journal of Chemistry (1983), vol. 36, pages 135-147, describes the reaction between methylhydrazine and ethyl 2-(ethoxymethylidene)-3-oxobutanoate in diethyl ether, which leads to the formation of ethyl 1,3-dimethyl-1H-pyrazole-4-carboxylate in a mixture with 10% of the 1,4,5-substituted regioisomer and an overall yield to the two isomers of 94%. When $R_a$ represents an alkyl group, the preparation of the 1,3,4-substituted pyrazoles can also be effected by the reaction of a suitable derivative of acrylic acid with hydrazine, followed by an alkylation reaction with a compound having formula $R_a$-LG, wherein LG represents an outgoing group such as a halogen, for example, for introducing the alkyl group onto the nitrogen atom in position 1, as indicated in the reaction scheme B:

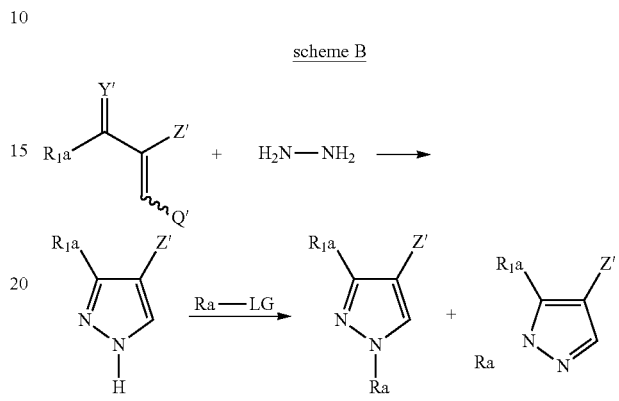

scheme B

As can be seen however, also in this case, the N-alkylation reaction of the pyrazoles is not regioselective and leads to the formation of mixtures of two pyrazole isomers, as described, for example, in the Australian Journal of Chemistry (1983), vol. 36, pages 135-147, in which the reaction of ethyl 3-methyl-1H-pyrazole-4-carboxylate with methyl iodide in ethanol leads to the formation of ethyl 1,3-dimethyl-1H-pyrazole-4-carboxylate in a 1:1 mixture with the 1,4,5-substituted regioisomer.

In Tetrahedron Letters (2009), vol. 50, pages 696-699, a regioselective synthesis is described, of derivatives of 3-substituted 1-methylpyrazole-4-carboxylic acids starting from 1,3-difunctionalized compounds such as β-ketoesters or β-ketoamides, by heating to reflux temperature with 1-formyl-1-methylhydrazine and subsequent cyclization with sodium ethylate at reflux temperature.

This procedure, however, has the disadvantage of having low yields, of around 48%.

The applicant has now surprisingly found that by reacting an intermediate having general formula (II)

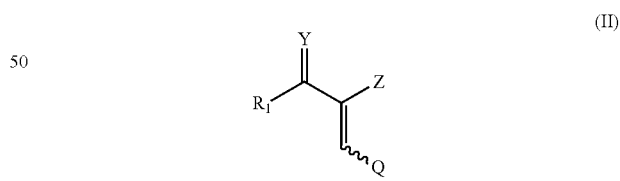

(II)

wherein $R_1$, Y, Z and Q have the meanings defined hereunder, with a 1,2-di-substituted hydrazine having general formula (III), in free or salified form,

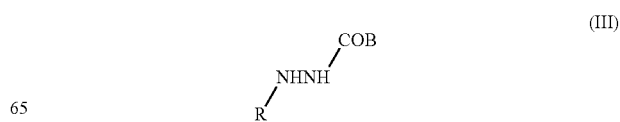

(III)

wherein R has the meanings defined hereunder, and the second nitrogen atom is bound to a carbonyl group CO suitably substituted, in the presence of an inorganic or organic acid which is added to the reaction mixture, the 1,3,4-substituted pyrazole having general formula (I) is obtained

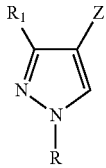

wherein R, R₁ and Z have the meanings defined hereunder, with a high yield and regioselectivity.

An object of the present invention therefore relates to a process for the synthesis of pyrazoles having general formula (I)

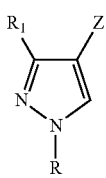

comprising the following steps:
i) a compound of general formula (II)

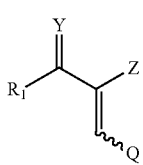

and a 1,2-di-substituted hydrazine of general formula (III)

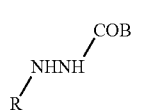

are mixed to form a reaction intermediate having a general formula (IV)

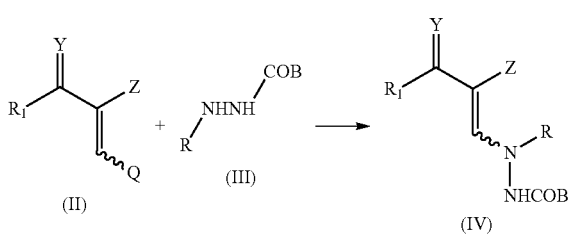

ii) the reaction mixture obtained in step i), in an acidic environment, cyclizes to form a pyrazole of general formula (I), according to reaction scheme 1

Scheme 1

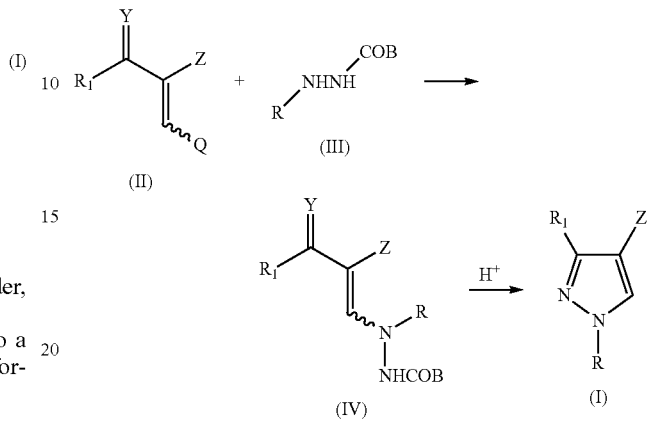

wherein in said formulae:

R represents a $C_1$-$C_6$ alkyl group or a $C_1$-$C_6$ haloalkyl group, said groups being optionally substituted with one or more groups selected from R', OR', $S(O)_n$R'; or R represents a $C_3$-$C_6$ cycloalkyl group, a $C_4$-$C_9$ cycloalkylalkyl group, a $C_2$-$C_6$ alkenyl group, a $C_2$-$C_6$, alkinyl group, a $C_6$-$C_{10}$ aryl group, a $C_7$-$C_{12}$ arylalkyl group, a heterocyclic ring with 5 or 6 atoms containing from 1 to 3 heteroatoms selected from N, O, S, all these groups being optionally substituted by one or more groups selected from halogen atoms, R', OR', NR'R", $S(O)_m$R', CONR'R", COR', $CO_2$R', CN, $NO_2$;

$R_1$ represents a $C_1$-$C_6$ alkyl group or a $C_1$-$C_6$ haloalkyl group, said groups being optionally substituted with one or more groups selected from R', OR', $S(O)_n$R'; or $R_1$ represents a $C_3$-$C_6$ cycloalkyl group, a $C_4$-$C_9$ cycloalkylalkyl group, a $C_6$-$C_{10}$ aryl group, a $C_7$-$C_{12}$ arylalkyl group, all these groups being optionally substituted by one or more groups selected from halogen atoms, R', OR', $S(O)_m$R', NR'R", CONR'R", COR', $CO_2$R', $NO_2$, CN;

Z represents a $CO_2R_2$ group, a $CONR_3R_4$ group or a CN group;

$R_2$ represents a $C_1$-$C_6$ alkyl group, a $C_1$-$C_6$ haloalkyl group, said groups being optionally substituted with one or more groups selected from R', OR', SR'; or $R_2$ represents a $C_3$-$C_6$ cycloalkyl group, a $C_4$-$C_9$ cycloalkylalkyl group, a $C_6$-$C_{10}$ aryl group, a $C_7$-$C_{12}$ arylalkyl group, all these groups being optionally substituted by one or more groups selected from halogen atoms, R', OR', $S(O)_m$R', NR'R", CONR'R", COR', $CO_2$R';

$R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, a $C_3$-$C_6$ cycloalkyl group, a $C_4$-$C_9$, cycloalkylalkyl group, a $C_2$-$C_6$ alkenyl group, a $C_2$-$C_6$ alkinyl group, a heterocyclic ring with 5 or 6 atoms, containing from 1 to 3 heteroatoms selected from N, O, S, all these groups being optionally substituted by one or more groups selected from halogen atoms, R', OR', NR'R", $S(O)_m$R', CONR'R", COR', $CO_2$R', CN, $NO_2$; or $R_3$ and $R_4$, together with the nitrogen atom to which they are bound, represent a heterocyclic nitrogenated ring with 5 or 6 atoms;

Y represents an oxygen or sulphur atom;

Q represents an $OR_5$, a $SR_5$, a $NR_6R_7$ group;

$R_5$ represents a $C_1$-$C_6$ alkyl group, optionally substituted with one or more groups selected from halogen atoms, R', OR', SR'; or $R_5$ represents a $C_3$-$C_6$ cycloalkyl group, a $C_6$-$C_{10}$ aryl group, a $C_7$-$C_{12}$ arylalkyl group, all these groups being optionally substituted by one or more groups selected from halogen atoms, R', OR', $S(O)_mR'$, NR'R", CONR'R", COR', $CO_2R$;

$R_6$ and $R_7$, equal to or different from each other, represent a hydrogen atom, a $C_1$-$C_6$ alkyl group, a $C_6$-$C_{10}$ aryl group, a $C_7$-$C_{12}$ arylalkyl group; or $R_6$ and $R_7$, together with the nitrogen atom to which they are bound, represent heterocyclic nitrogenated ring with 5 or 6 atoms;

B represents a $R_8$, $OR_9$ or $NR_{10}R_{11}$ group;

$R_8$ and $R_9$ represent a $C_1$-$C_6$ alkyl group, a $C_2$-$C_6$ alkenyl group, a $C_3$-$C_6$ cycloalkyl group, a $C_6$-$C_{10}$ aryl group, a $C_7$-$C_{12}$ arylalkyl group, a heterocyclic ring with 5 or 6 atoms, containing from 1 to 3 heteroatoms selected from N, O, S, all these groups being optionally substituted by one or more groups selected from halogen atoms, R', OR', NR'R", $S(O)_mR'$, CONR'R", COR', $CO_2R'$, CN;

$R_{10}$ and $R_{11}$, equal to or different from each other, represent a hydrogen atom, a $C_1$-$C_6$ alkyl group, a $C_6$-$C_{10}$ aryl group, a $C_7$-$C_{12}$ arylalkyl group, said groups being optionally substituted with one or more halogen atoms; or $R_{10}$ and $R_{11}$, together with the nitrogen atom to which they are bound, can represent a heterocyclic nitrogenated ring with 5 or 6 atoms;

R' and R" represent a hydrogen atom, a $C_1$-$C_4$ alkyl group, a $C_1$-$C_4$ haloalkyl group;

m represents 0, 1 or 2.

Examples of a $C_1$-$C_6$ alkyl group are methyl, ethyl, propyl, butyl, pentyl, hexyl.

Examples of a $C_1$-$C_6$ haloalkyl group are dichloromethyl, difluoromethyl, trichloromethyl, trifluoromethyl, chloro-difluoromethyl, dichloroethyl, trifluoroethyl, tetrafluoroethyl, pentafluoroethyl, tetrafluoropropyl, pentafluoropropyl, dichlorobutyl, difluorobutyl, dichloropentyl, difluoropentyl, dichlorohexyl, difluorohexyl.

Examples of a $C_3$-$C_6$ cycloalkyl group are cyclopropyl, cyclobutyl, cyclopentyl, cyclohexyl.

Examples of a $C_4$-$C_9$ cycloalkylalkyl group are cyclopropylmethyl, cyclobutylmethyl, cyclopentylmethyl, cyclohexylmethyl, cyclohexylethyl, cyclohexylpropyl.

Examples of a $C_2$-$C_6$ alkenyl group are ethenyl, propenyl, butenyl, pentenyl, hexenyl.

Examples of a $C_2$-$C_6$ alkinyl group are ethinyl, propinyl, butinyl, pentinyl, hexinyl.

Examples of a $C_6$-$C_{10}$ aryl group are phenyl, naphthyl.

Examples of a $C_7$-$C_{12}$ arylalkyl group are benzyl, phenylethyl, phenylpropyl, phenylbutyl, phenylpentyl, phenylhexyl, naphthylmethyl, naphthylethyl.

Examples of a heterocyclic ring with 5 or 6 atoms containing from 1 to 3 heteroatoms selected from N, O, S, are pyrrolyl, pyrazolyl, imidazolyl, triazolyl, thiadiazolyl, oxadiazolyl, furanyl, thiophenyl, pyridyl, pyrimidyl, triazinyl.

Examples of a heterocyclic nitrogenated ring with 5 or 6 atoms are pyrrolidyl, piperidyl, morpholyl.

Examples of halogen atoms are fluorine, chlorine, bromine, iodine.

Among the pyrazoles having general formula (I) that can be prepared with the process of the present invention, preferred are those wherein:

R represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;

$R_1$ represents a $C_1$-$C_6$ alkyl group, a $C_1$-$C_6$ haloalkyl group, or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;

Z represents a $CO_2R_2$ group, a $CONR_3R_4$ group;

$R_2$ represents a $C_1$-$C_6$ alkyl group or a $C_1$-$C_6$ haloalkyl group; or it represents a $C_6$-$C_{10}$ aryl group, a $C_7$-$C_{12}$ arylalkyl group, said groups being optionally substituted by one or more groups selected from halogen atoms, R', OR';

$R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, each of these groups, in turn, being optionally substituted by one or more groups selected from halogen atoms, R', OR'; or $R_3$ and $R_4$, together with the nitrogen atom to which they are bound, represent a heterocyclic nitrogenated ring with 5 or 6 atoms;

R' and R" represent a hydrogen atom, a $C_1$-$C_4$ alkyl group, a $C_1$-$C_4$ haloalkyl group.

Particularly preferred are products having formula (I) wherein:

R represents a $C_1$-$C_6$ alkyl group or a phenyl optionally substituted with halogen atoms;

$R_1$ represents a methyl, a difluoromethyl, a trifluoromethyl or a phenyl optionally substituted with halogen atoms;

Z represents a $CO_2R_2$ group wherein $R_2$ represents a $C_1$-$C_6$ alkyl or haloalkyl group.

Even more preferred is a process according to the present invention for the synthesis of products having general formula (I) wherein:

R represents a methyl;

$R_1$ represents a methyl, a difluoromethyl, a trifluoromethyl;

Z represents a $CO_2R_2$ group wherein $R_2$ represents a $C_1$-$C_6$ alkyl or haloalkyl group.

As previously indicated, the process, object of the present invention, is effected in two consecutive steps.

Initially, the condensation takes place of the compound having general formula (II) with the 1,2-disubstituted hydrazine having general formula (III) and more specifically having formula (III-a), (III-b) or (III-c)

(III-a)

(III-b)

(III-c)

to give an open intermediate having general formula (IV-a), (IV-b), (IV-c) respectively, which is normally not isolated and which cyclizes, in an acid environment, to give the pyrazole having formula (I), according to the reaction scheme 2-a, 2-b or 2-c:

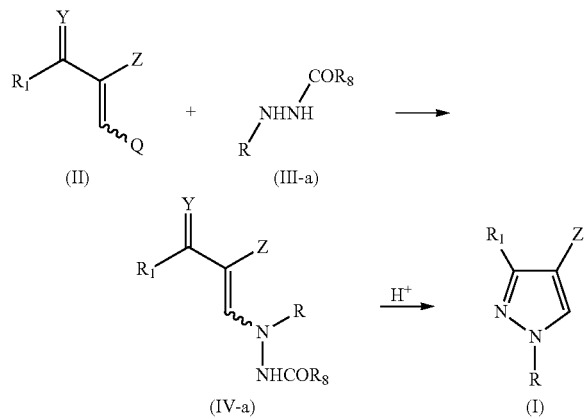

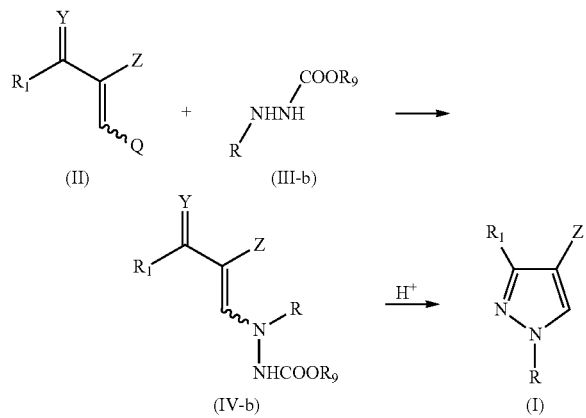

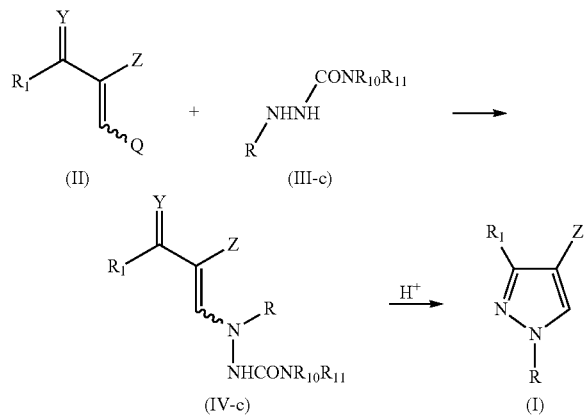

wherein R, $R_1$, $R_8$, $R_9$, $R_{10}$, $R_{11}$, Y, Z, Q have the meanings described above.

The reaction between the compound having general formula (II) and the compound having general formula (III) can be effected by simply mixing the two reagents, but it is preferably carried out in the presence of an organic solvent at a temperature ranging from −20° C. to the boiling temperature of the reaction mixture; a temperature range from −10° C. to 80° C. is particularly preferred for obtaining a high regioselectivity.

Examples of solvents that can be used for the above-mentioned reaction comprise aliphatic or cycloaliphatic hydrocarbons (petroleum ether, hexane, cyclohexane etc.), chlorinated hydrocarbons (methylene chloride, chloroform, carbon tetrachloride, dichloroethane, etc.), aromatic hydrocarbons (benzene, toluene, xylene, chlorobenzene, etc.), ethers (diethyl ether, diisopropyl ether, dimethoxyethane, dioxane, tetrahydrofuran, etc.), alcohols and glycols (methanol, ethanol, iso-propanol, methylcellosolve, ethylene glycol, etc.), ketones (acetone, methylethylketone, methylpropylketone, methylisobutyl-ketone, etc.), nitriles (acetonitrile, benzonitrile, etc.), aprotic dipolar solvents (dimethylformamide, dimethylacetamide, hexamethylphosphoric triamide, sulfoxide, sulfolane, N-methyl-pyrrolidone, etc.).

Among these, aromatic hydrocarbons such as toluene and xylene, chlorinated hydrocarbons such as methylene chloride, and dichloroethane, alcohols such as methanol, ethanol and iso-propanol, tetrahydrofuran, dimethylformamide, are preferred.

Toluene, dichloroethane (DCE), dichloromethane (DCM) and ethanol are particularly preferred.

The reaction is normally carried out at atmospheric pressure but can also be carried out at reduced pressure or under pressure.

The reaction can be carried out by the reaction of 1 mole of compound having general formula (II) with a quantity of compound having general formula (III) which ranges from 0.8 to 3 moles, preferably from 0.8 to 1.5 moles and more preferably with an approximately equimolar quantity of the two reagents.

The acid environment which allows the cyclization of the intermediate (IV) to give the pyrazole having formula (I), can be obtained by the addition of an inorganic or organic acid in step (ii) starting from a compound (III) in free form or with the use, as starting compound, of a compound (III) salified with an inorganic or organic acid.

In the first embodiment of the process according to the present invention, an organic or inorganic acid is added to the reaction mixture obtained in step (i) at a temperature ranging from −10° C. to the boiling point of the reaction mixture, preferably at a temperature ranging from 0° C. to 40° C. The use of strong inorganic or organic acids is preferable, either concentrated or suitably diluted.

Acids suitable for the purpose are, for example, HCl, HBr, $H_2SO_4$, $CF_3CO_2H$, $CH_3SO_3H$, $CF_3SO_3H$, p-toluenesulfonic acid; more preferably HCl, HBr and $H_2SO_4$.

In step (ii), from 0.01 to 10 moles of acid, preferably from 0.05 to 5 moles and more preferably from 0.1 to 1.5 moles of acid are used with respect to the compound having formula (III).

In the second embodiment of the process according to the present invention, the compound having formula (III) is used in salified form with an organic or inorganic acid. The acidity necessary for favouring the cyclization is therefore already present in the reaction environment and the subsequent addition of acid is generally not necessary.

When the reaction has been completed, the pyrazoles having formula (I) can be isolated and purified according to methods known in the practice of organic chemistry, on both a laboratory scale and in industrial plants. The reaction mixture, for example, can be diluted with water and extracted with an organic solvent slightly miscible or immiscible with water, and the desired pyrazole recovered by evaporation of the organic solvent.

The starting compounds having general formula (II) and (III), when they are not already known per se, can be easily prepared according to methods known in organic chemical practice.

The compounds having general formula (II) can be prepared, for example, according to what is described in "Organic and Biomolecular Chemistry" (2009), vol. 7, pages 2182-2186; Bioorganic & Medicinal Chemistry Letters (2005), vol. 15, pages 4370-4374.

Preferred compounds having general formula (II) for the process according to the present invention are those wherein:
  $R_1$ represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;
  Z represents a $CO_2R_2$ group, a $CONR_3R_4$ group;
  $R_2$ represents a $C_1$-$C_6$ alkyl group or a $C_1$-$C_6$ haloalkyl group; or it represents a $C_6$-$C_{10}$ aryl group, a $C_7$-$C_{12}$ arylalkyl group, these groups being optionally substituted by one or more groups selected from halogen atoms, R', OR';
  $R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, each of these groups, in turn, being optionally substituted by one or more groups selected from halogen atoms, R', OR'; or $R_3$ and $R_4$, together with the nitrogen atom, represent a heterocyclic nitrogenated ring with 5 or 6 atoms;
  R' and R" represent a hydrogen atom, a $C_1$-$C_4$ alkyl group, a $C_1$-$C_4$ haloalkyl group;
  Y represents an oxygen atom;
  Q represents an $OR_5$ group;
  $R_5$ represents a $C_1$-$C_6$ alkyl group.

When the compounds having general formula (III) are not commercially available, they can be prepared according to the procedures described, for example, in "Chemical Communications" (2012), vol. 48, pages 5772-5774; "Journal of Organic Chemistry" (1972), vol. 37, pages 3608-3615; U.S. Pat. No. 6,083,908; U.S. Pat. No. 4,045,484 (III-a); "Angewandte Chemie International Edition" (2013), vol. 52, pages 4613-4617; "Journal of American Chemical Society" (1971), vol. 93, pages 1992-1999; patent DE 951503 (III-b); "Acta Chemica Scandinavica, Series B: Organic Chemistry and Biochemistry" (1977), vol. 31, pages 145-148 (III-c).

Preferred compounds having general formula (III) for the process according to the present invention are those wherein:
  R represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;
  B represents a $R_8$, $OR_9$ or $NR_{10}R_{11}$ group;
  $R_8$ represents a $C_1$-$C_6$ alkyl group, possibly substituted with halogen atoms, or a $C_6$-$C_{10}$ aryl group;
  $R_9$ represents a $C_1$-$C_6$ alkyl group, possibly substituted with halogen atoms, or a $C_6$-$C_{10}$ aryl group;
  $R_{10}$ and $R_{11}$, equal to or different from each other, represent H, a $C_1$-$C_6$ alkyl group, a $C_6$-$C_{10}$ aryl group.

The intermediates having general formula (IV) are not described in literature. As already specified, they are not normally isolated and are cyclized directly in the reaction environment to give pyrazoles having formula (I). If necessary, however, they can be isolated and purified according to methods known in organic chemistry, on both a laboratory scale and in industrial plants.

Particularly preferred is a process for the synthesis of pyrazoles having general formula (I) wherein:
  R represents a methyl;
  $R_1$ represents a methyl, a difluoromethyl, a trifluoromethyl;
  Z represents a $CO_2R_2$ group, wherein $R_2$ represents a $C_1$-$C_6$ alkyl or haloalkyl group, wherein step (i) is carried out at a temperature ranging from −10° C. a 80° C., in an organic solvent, with an equimolar quantity of compounds having general formula (II) and (III) and step (ii) is carried out in an acid environment at a temperature ranging from 0° C. to 40° C.

Step (ii) preferably comprises the addition of an acid selected from HCl, HBr or $H_2SO_4$ in a molar ratio ranging from 0.1 to 1.5 with respect to the compound having formula (III).

In particular, the intermediates having general formula (IV) are of great applicative interest, and consequently a further object of the present invention relates to intermediates having general formula (IV)

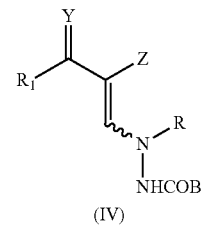

(IV)

wherein:
  R represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;
  $R_1$ represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;
  Z represents a $CO_2R_2$ group, a $CONR_3R_4$ group;
  $R_2$ represents a $C_1$-$C_6$ alkyl group or a $C_1$-$C_6$ haloalkyl group; or it represents a $C_6$-$C_{10}$ aryl group, a $C_7$-$C_{12}$ arylalkyl group, these groups being optionally substituted by one or more groups selected from halogen atoms, R', OR';
  $R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, each of these groups in turn being optionally substituted by one or more groups selected from halogen atoms, R', OR'; or $R_3$ and $R_4$, together with the nitrogen atom to which they are bound, represent a heterocyclic nitrogenated ring with 5 or 6 atoms;

R' and R" represent a hydrogen atom, a $C_1$-$C_4$ alkyl group, a $C_1$-$C_4$ haloalkyl group;

Y represents an oxygen atom;

B represents a $R_8$, $OR_9$ or $NR_{10}R_{11}$ group;

$R_8$ represents a $C_1$-$C_6$ alkyl group optionally substituted with halogen atoms, or a $C_6$-$C_{10}$ aryl group;

$R_9$ represents a $C_1$-$C_6$ alkyl group optionally substituted with halogen atoms, or a $C_6$-$C_{10}$ aryl group;

$R_{10}$ and $R_{11}$, equal to or different from each other, represent H, a $C_1$-$C_6$ alkyl group, a $C_6$-$C_{10}$ aryl group.

Preferred intermediate compounds are intermediate compounds which are formed in step (i) starting from preferred starting compounds having formula (II) and (III).

Particularly preferred are intermediates having formula (IV) wherein:

R represents a methyl;

$R_1$ represents a methyl, a difluoromethyl, a trifluoromethyl;

Z represents a $CO_2R_2$ group, wherein $R_2$ represents a $C_1$-$C_6$ alkyl or haloalkyl group, B represents a $R_8$, $OR_9$ or $NR_{10}R_{11}$ group;

$R_8$ represents a $C_1$-$C_6$ alkyl group optionally substituted with halogen atoms, or a $C_6$-$C_{10}$ aryl group;

$R_9$ represents a $C_1$-$C_6$ alkyl group optionally substituted with halogen atoms, or a $C_6$-$C_{10}$ aryl group;

$R_{10}$ and $R_{11}$, equal to or different from each other, represent H, a $C_1$-$C_6$ alkyl group, a $C_6$-$C_{10}$ aryl group.

There are numerous advantages of the process of the present invention.

In addition to the regioselectivity, the reaction is carried out under conditions that can be easily produced in both a laboratory and in industrial plants.

Operating under the conditions described in the present invention, derivatives of 1,3-disubstituted 4-pyrazolecarboxylic acids can be obtained with optimum yields and a high purity, which can be used in the synthesis of products extremely useful in both the pharmaceutical and agrochemical fields.

The following examples are provided for illustrative purposes of the present invention and should be considered as being descriptive and non-limiting of the same.

EXAMPLE 1

Preparation of ethyl 1-isopropyl-3-methyl-1H-pyrazole-4-carboxylate (compound nr. 1.1)

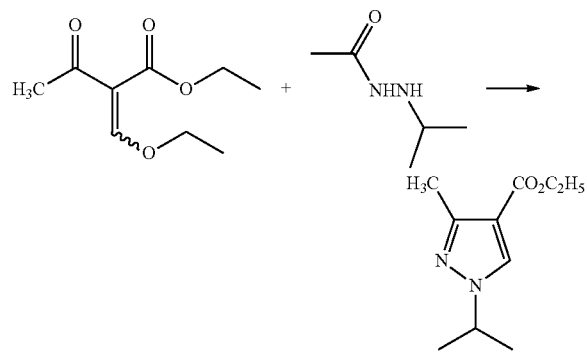

Ethyl 2-(ethoxymethylidene)-3-oxybutanoate (2.0 g) dissolved in 5 ml of ethanol is added dropwise to a solution of N'-isopropylacetohydrazide (1.24 g) in 14 ml of ethanol, cooled to 0° C. The whole mixture is left overnight under stirring at room temperature.

2 ml of $H_2SO_4$ at 96% are then added and the mixture is stirred for 15 minutes at room temperature.

Ethyl acetate and water are added at the end of the reaction, the phases are separated and the aqueous phase is extracted twice with ethyl acetate. The joined organic phases are washed with water, then with a saturated solution of NaCl, anhydrified with $Na_2SO_4$ and concentrated under vacuum. 1.93 g of a product is obtained, in the form of an oil, with a regioselectivity >99%.

The raw product is then purified by silica gel flash chromatography, eluting with n-heptane/ethyl acetate 7:3. 1.73 g of pure product are obtained (yield: 83%).

$^1$H-NMR (CDCl$_3$): δ 1.30 (t, 3H, CH$_3$ ethyl), 1.47 (2 d, 6H, CH$_3$ isopropyl), 2.40 (s, 3H, CH$_3$), 4.20 (q, 2H, CH$_2$ ethyl), 4.30-4.41 (m, 1H, CH isopropyl), 7.80 (s, 1H, H arom.).

EXAMPLE 2

Preparation of ethyl 1,3-dimethyl-1H-pyrazole-4-carboxylate (compound nr. 2.1)

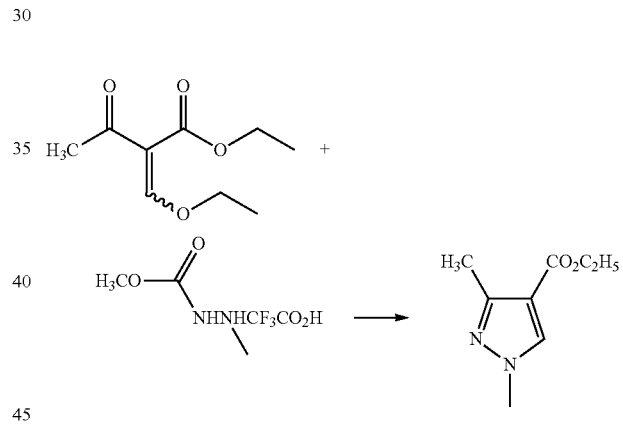

A solution of methyl 2-methylhydrazinecarboxylate trifluoroacetate (0.91 g) dissolved in 5 ml of toluene is added to a solution of ethyl 2-(ethoxymethylidene)-3-oxybutanoate (1.06 g) in 5 ml of toluene, kept at a temperature ranging from 0 to 10° C. The whole mixture is left to reach room temperature and is kept under stirring at this temperature for 3 hours.

At the end of the reaction, the mixture is poured into water and extracted three times with ethyl acetate. The joined organic phases are washed with water, then with a saturated solution of NaCl and finally anhydrified with $Na_2SO_4$ and evaporated under vacuum.

0.63 g of product is obtained, in solid form, (yield 77%, regioselectivity >99%). MP: 48-49° C.

$^1$H-NMR (CDCl$_3$): δ 1.32 (t, 3H, CH$_3$ ethyl), 2.43 (s, 3H, CH$_3$), 3.82 (s, 3H, CH$_3$), 4.25 (q, 2H, CH$_2$ ethyl), 7.77 (s, 1H, H arom.)

EXAMPLE 3

Preparation of ethyl 1-phenyl-3-trifluoromethyl-1H-pyrazole-4-carboxylate (compound 3.1)

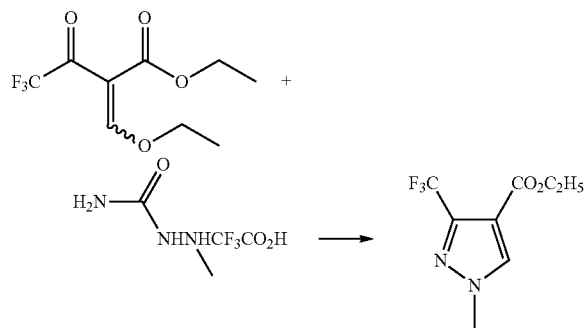

A solution of ethyl 2-(ethoxymethylidene)-4,4,4-trifluoro-3-oxobutanoate (0.96 g) in 3 ml of ethanol is rapidly added dropwise to a suspension of 2-methylhydrazinecarboxamide chlorohydrate (0.5 g) in 7 ml of ethanol and is left to react at room temperature, under stirring, overnight.

At the end of the reaction the mixture is cooled to 0° C. and 3 ml of 10% HCl are added, it is then diluted with ethyl acetate and a saturated solution of NaCl. The phases are separated and the organic phase is anhydrified with $Na_2SO_4$ and evaporated under vacuum.

0.69 g of product are obtained, in solid form (yield: 78%, regioselectivity >99%). M.P.: 53-54° C.

$^1$H-NMR ($CDCl_3$): δ 1.3 (t, 3H, $CH_3$ ethyl), 3.95 (s, 3H, $CH_3$), 4.3 (q, 2H, $CH_2$ ethyl), 7.95 (s, 1H, H arom.)

EXAMPLE 4

Following the procedure described in the previous example 1, the compounds listed in Table 1 were prepared, identified by means of $^1$H-NMR indicated in Table 2.

EXAMPLE 5

Following the procedure described in the previous example 2, the compounds listed in Table 3 were prepared, identified by means of $^1$H-NMR indicated in Table 4.

EXAMPLE 6

Following the procedure described in the previous example 3, the compounds listed in Table 5 were prepared, identified by means of $^1$H-NMR indicated in Table 6.

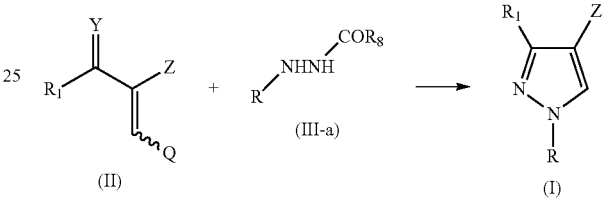

EXAMPLE 4

TABLE 1

| Compound No | $R_1$ | Y | Z | Q | R | $R_8$ | III-a·HX | Solvent | T (° C.) | Yield(%); rs (%)* |
|---|---|---|---|---|---|---|---|---|---|---|
| 1.2 | $CF_3$ | O | $CO_2C_2H_5$ | $C_2H_5O$ | iPr | $CH_3$ | — | toluene | r.t. | 80; >99 |
| 1.3 | Ph | O | $CO_2C_2H_5$ | $C_2H_5O$ | iPr | $CH_3$ | — | toluene | r.t. | 82; >99 |
| 1.4 | $CHF_2$ | O | $CO_2C_2H_5$ | $C_2H_5O$ | iPr | $CH_3$ | — | ethanol | r.t. | 83; >99 |
| 1.5 | $CH_3$ | O | $CO_2C_2H_5$ | $C_2H_5O$ | $CH_3$ | $CH_3$ | $CF_3CO_2H$ | toluene | r.t. | 88; 98 |
| 1.6 | Ph | O | $CO_2C_2H_5$ | $C_2H_5O$ | $CH_3$ | $CH_3$ | $CF_3CO_2H$ | DCE | r.t. | 85; >99 |
| 1.7 | $CHF_2$ | O | $CO_2C_2H_5$ | $C_2H_5O$ | $CH_3$ | $CH_3$ | $CF_3CO_2H$ | DCM | 40 | 95; >99 |

*rs % represents the selectivity in the regioisomer (I)

EXAMPLE 4

TABLE 2

| Compound No | Physical aspect | PF (° C.) | $^1$H-NMR ($CDCl_3$) δ (ppm) |
|---|---|---|---|
| 1.2 | oil | — | 1.33 (t, 3H, $CH_3$ ethyl), 1.52 (2d, 6H, $CH_3$ isopropyl), 4.30 (q, 2H, $CH_2$ ethyl), 4.46-4.60 (m, 1H, CH isopropyl), 8.00 (s, 1H, H arom.) |
| 1.3 | oil | — | 1.27 (t, 3H, $CH_3$ ethyl), 1.55 (2d, 6H, $CH_3$ isopropyl), 4.24 (q, 2H, $CH_2$ ethyl), 4.46-4.60 (m, 1H, CH isopropyl), 7.30-7.45 (m, 3H, H arom.), 7.73-7.85 (m, 2H, H arom.), 8.00 (s, 1H, H arom.) |
| 1.4 | oil | — | 1.30 (t, 3H, $CH_3$ ethyl), 1.50 (2d, 6H, $CH_3$ isopropyl), 4.29 (q, 2H, $CH_2$ ethyl), 4.49-4.58 (m, 1H, CH isopropyl), 7.05 (t, 1H, CHF2), 7.90 (s, 1H, H arom.) |
| 1.5 | solid | 48-49 | 1.32 (t, 3H, $CH_3$ ethyl), 2.43 (s, 3H, $CH_3$), 3.82 (s, 3H, $CH_3$), 4.25 (q, 2H, $CH_2$ ethyl), 7.77 (s, 1H, H arom.) |
| 1.6 | solid | 72-73 | 1.25 (t, 3H, $CH_3$ ethyl), 3.93 (s, 3H, $CH_3$), 4.23 (q, 2H, $CH_2$ ethyl), 7.32-7.44 (m, 3H, H arom.), 7.71-7.80 (m, 2H, H arom.), 7.94 (s, 1H, H arom.) |
| 1.7 | solid | 60-61 | 1.40 (t, 3H, $CH_3$ ethyl), 3.95 (s, 3H, $CH_3$), 4.35 (q, 2H, $CH_2$ ethyl), 7.10 (t, 1H, $CHF_2$), 7.90 (s, 1H, H arom.) |

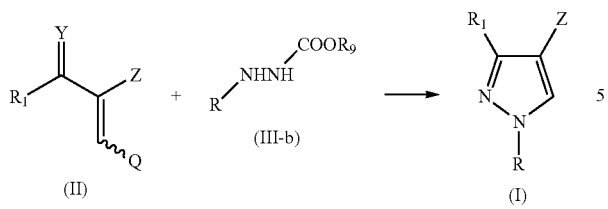

EXAMPLE 5

TABLE 3

| Compound No | $R_1$ | Y | Z | Q | R | $R_9$ | III-b•HX | Solvent | T (°C.) | Yield (%), rs (%)* |
|---|---|---|---|---|---|---|---|---|---|---|
| 2.2 | $CF_3$ | O | $CO_2C_2H_5$ | $C_2H_5O$ | $CH_3$ | $CH_3$ | $CF_3CO_2H$ | toluene | r.t. | 83, >99 |
| 2.3 | Ph | O | $CO_2C_2H_5$ | $C_2H_5O$ | $CH_3$ | $CH_3$ | $CF_3CO_2H$ | toluene | r.t. | 75, >99 |
| 2.4 | $CHF_2$ | O | $CO_2C_2H_5$ | $C_2H_5O$ | $CH_3$ | $CH_3$ | $CF_3CO_2H$ | ethanol | r.t. | 95, >99 |
| 2.5 | $CH_3$ | O | $CO_2C_2H_5$ | $C_2H_5O$ | Ph | $CH_3$ | — | DCM | 40 | 80, >99 |
| 2.6 | $CF_3$ | O | $CO_2C_2H_5$ | $C_2H_5O$ | Ph | $CH_3$ | — | DCE | 80 | 75, >99 |
| 2.7 | Ph | O | $CO_2C_2H_5$ | $C_2H_5O$ | Ph | $CH_3$ | — | DCE | 80 | 87, >99 |
| 2.8 | $CHF_2$ | O | $CO_2C_2H_5$ | $C_2H_5O$ | Ph | $CH_3$ | — | DCE | r.t. | 89, >99 |
| 2.9 | 4-ClPh | O | $CO_2C_2H_5$ | $C_2H_5O$ | Ph | $CH_3$ | — | DCE | 80 | 88, >99 |
| 2.10 | $CF_3$ | O | $CO_2C_2H_5$ | $C_2H_5O$ | 4-ClPh | $CH_3$ | — | DCE | 80 | 78, >99 |

*rs % represents the regioselectivity in the isomer (I)

EXAMPLE 5

TABLE 4

| Compound No | Physical appearance | Melting point (°C.) | $^1$H-NMR (CDCl$_3$) δ (ppm) |
|---|---|---|---|
| 2.2 | solid | 53-54 | 1.3 (t, 3H, CH$_3$ ethyl), 3.95 (s, 3H, CH$_3$), 4.3 (q, 2H, CH$_2$ ethyl), 7.95 (s, 1H, H arom.) |
| 2.3 | solid | 72-73 | 1.25 (t, 3H, CH$_3$ ethyl), 3.93 (s, 3H, CH$_3$), 4.23 (q, 2H, CH$_2$ ethyl), 7.32-7.44 (m, 3H, H arom.), 7.71-7.80 (m, 2H, H arom.), 7.94 (s, 1H, H arom.) |
| 2.4 | solid | 60-61 | 1.40 (t, 3H, CH$_3$ ethyl), 3.95 (s, 3H, CH$_3$), 4.35 (q, 2H, CH$_2$ ethyl), 7.10 (t, 1H, CHF$_2$), 7.90 (s, 1H, H arom.) |
| 2.5 | solid | 52-53 | 1.48 (t, 3H, CH$_3$ ethyl), 2.56 (s, 3H, CH$_3$), 4.35 (q, 2H, CH$_2$ ethyl), 7.26-7.70 (m, 5H, H arom.), 8.35 (s, 1H, H arom.) |
| 2.6 | solid | 72-73 | 1.4 (t, 3H, CH$_3$ ethyl), 4.4 (q, 2H, CH$_2$ ethyl), 7.4-7.8(m, 5H, H arom.), 8.50 (s, 1H, H arom.) |
| 2.7 | solid | 88-89 | 1.3 (t, 3H, CH$_3$ ethyl), 4.3 (q, 2H, CH$_2$ ethyl), 7.30-7.95 (m, 10H, H arom.), 8.50(s, 1H, arom) |
| 2.8 | solid | 79-80 | 1.48 (t, 3H, CH$_3$ ethyl), 4.38 (q, 2H, CH$_2$ ethyl), 7.20 (t, 1H, CHF$_2$), 7.26-7.70 (m, 5H, arom.), 8.40 (s, 1H, H arom.) |
| 2.9 | solid | 144-146 | 1.34 (t, 3H, CH$_3$ ethyl), 4.30 (q, 2H, CH$_2$ ethyl), 7.35 (m, 1H, H arom.), 7.40(m, 2H, H arom.), 7.50 (m, 2H, H arom.), 7.75 (m, 2H, H arom.), 7.90 (m, 2H, H arom.), 8.50 (s, 1H, H arom.) |
| 2.10 | solid | 53-54 | 1.39 (t, 3H, CH$_3$ ethyl), 4.35 (q, 2H, CH$_2$ ethyl), 7.50 (m, 2H, H arom.), 7.65 (m, 2H, H arom.), 8.45 (s, 1H, H arom.) |

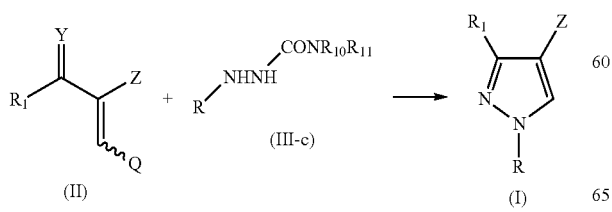

EXAMPLE 6

TABLE 5

| Compound No | R1 | Y | Z | Q | R | R10 | R11 | III-c•HX | Solvent | T (° C.) | Yield (%), rs (%)* |
|---|---|---|---|---|---|---|---|---|---|---|---|
| 3.2 | $CHF_2$ | O | $CO_2C_2H_5$ | $C_2H_5O$ | $CH_3$ | H | H | HCl | ethanol | r.t. | 95, >99 |
| 3.3 | $CH_3$ | O | $CO_2C_2H_5$ | $C_2H_5O$ | Ph | H | H | — | ethanol | r.t. | 82, 98 |
| 3.4 | $CF_3$ | O | $CO_2C_2H_5$ | $C_2H_5O$ | Ph | H | H | — | ethanol | r.t. | 85, >99 |
| 3.5 | Ph | O | $CO_2C_2H_5$ | $C_2H_5O$ | Ph | H | H | — | ethanol | 78 | 81, >99 |
| 3.6 | $CHF_2$ | O | $CO_2C_2H_5$ | $C_2H_5O$ | Ph | H | H | — | ethanol | r.t. | 87, >99 |

*rs % represents the regioselectivity in the isomer (I)

EXAMPLE 6

TABLE 6

| Compound No | Physical appearance | PF (° C.) | $^1$H-NMR ($CDCl_3$) δ (ppm) |
|---|---|---|---|
| 3.2 | solid | 60-61 | 1.40 (t, 3H, $CH_3$ ethyl), 3.95 (s, 3H, $CH_3$), 4.35 (q, 2H, $CH_2$ ethyl), 7.10 (t, 1H, $CHF_2$), 7.90 (s, 1H, H arom.) |
| 3.3 | solid | 52-53 | 1.48 (t, 3H, $CH_3$ ethyl), 2.56 (s, 3H, $CH_3$), 4.35 (q, 2H, $CH_2$ ethyl), 7.26-7.70 (m, 5H, arom.), 8.35 (s, 1H, H arom.) |
| 3.4 | solid | 72-73 | 1.4 (t, 3H, $CH_3$ ethyl), 4.4 (q, 2H, $CH_2$ ethyl), 7.4-7.8(m, 5H, H arom.), 8.50 (s, 1H, H arom.) |
| 3.5 | solid | 88-89 | 1.3 (t, 3H, $CH_3$ ethyl), 4.3 (q, 2H, $CH_2$ ethyl), 7.30-7.95 (m, 10H, H arom.), 8.50(s, 1H, H arom) |
| 3.6 | solid | 79-80 | 1.48 (t, 3H, CH3 ethyl), 4.38 (q, 2H, $CH_2$ ethyl), 7.20 (t, 1H, $CHF_2$), 7.26-7.70 (m, 5H, arom.), 8.40 (s, 1H, H arom.) |

EXAMPLE 7

Preparation of methyl 2-[2-(ethoxycarbonyl)-4,4-difluoro-3-oxobut-1-enyl]-2-methylhydrazinecarboxylate (intermediate IV-b: $R_1$=$CHF_2$, Y=O, Z=$CO_2C_2H_5$, R=$CH_3$, $R_9$=$CH_3$)

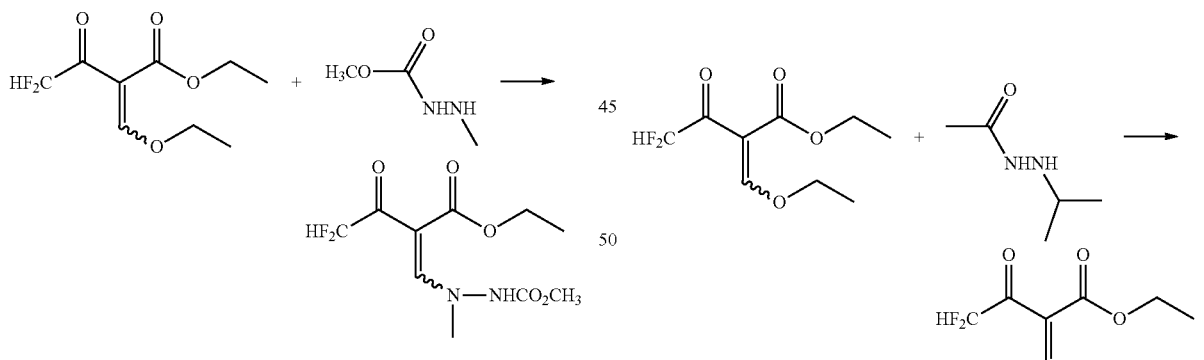

Ethyl 2-(ethoxymethylidene)-4,4-trifluoro-3-oxo-butanoate (2.14 g) dissolved in 6 ml of methylene chloride is added dropwise to a solution of methyl 2-methylhydrazinecarboxylate (1.0 g) in 12 ml of methylene chloride, cooled to 0° C. The mixture is left under stirring at room temperature.

After an hour the reaction mixture is concentrated under vacuum. 2.60 g of product are obtained, in solid form (yield:quantitative).

$^1$H-NMR ($CDCl_3$): mixture of E/Z isomers (70:30) determined on the basis of the signal of the C=C double bond δ 1.30 (t, 3H, $CH_3$ ethyl), 3.65 (s, 3H, $CO_2CH_3$), 4.25 (q, 2H, $CH_2$ ethyl), 6.35 and 6.80 (t, 1H, $CHF_2$), 8.00 and 8.25 (s, 1H, HC=C), 8.65 and 8.90 (s, 1H, NH)

EXAMPLE 8

Preparation of ethyl 3-(2-acetyl-1-isopropylhydrazine)-2-(difluoroacetyl)-acrylate (intermediate IV-a: $R_2$=$CHF_2$, Y=O, Z=$CO_2C_2H_5$, R=iPr, $R_8$=$CH_3$)

A suspension of N'-isopropylacetohydrazide (1.0 g) in 2-(ethoxymethylidene)-4.4-trifluoro-3-oxobutanoate (1.9 g) is left under stirring at room temperature.

The reaction mixture is initially transformed into a solution which solidifies with time. After a night, 2.51 g are obtained, in solid form (yield:quantitative).

$^1$H-NMR ($CDCl_3$): mixture of E/Z isomers (84:16) determined on the basis of the C=C double bond δ 1.30 (t, 3H, CH₃ ethylisopropyl), 1.40 (2 d, 6H, CH₃ isopropyl), 1.95 (s, 3H, COCH₃), 3.9-4.15 (m, 1H, CH isopropyl), 4.25 (q, 2H, CH₂ ethyl), 6.3 and 6.75 (t, 1H, CHF₂), 7.95 and 8.2 (s, 1H, HC=C), 8.6 and 8.85 (s, 1H, NH)

EXAMPLE 9

Comparative Test

Preparation of ethyl 1-methyl-3-trifluoromethyl-1H-pyrazole-4-carboxylate

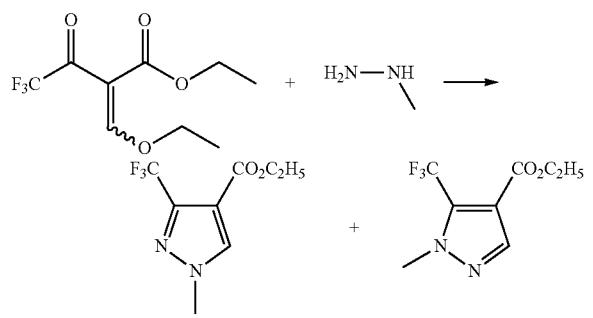

A solution of ethyl 2-(ethoxymethylidene)-4,4,4-trifluoro-3-oxobutanoate (1.0 g) in 5 ml of toluene is rapidly added dropwise to a solution of 1-methylhydrazine (0.25 g) in 5 ml of toluene, cooled to 10° C., and the mixture is left to react at room temperature, under stirring, overnight.

At the end of the reaction, the mixture is cooled to 0° C. and 0.5 ml of HCl at 10% are added. The phases are separated and the organic phase is first washed with fresh water and then with brine. The whole solution is anhydrified with Na₂SO₄ and the solvent is evaporated under reduced pressure.

0.85 g of raw product are obtained, in liquid form, containing an 87:13 mixture of ethyl 1-methyl-3-trifluoromethyl-1H-pyrazole-4-carboxylate and ethyl 1-methyl-5-trifluoromethyl-1H-pyrazole-carboxylate isomers.

EXAMPLE 10

Comparative Test

Preparation of ethyl 1-phenyl-3-methyl-1H-pyrazole-4-carboxylate

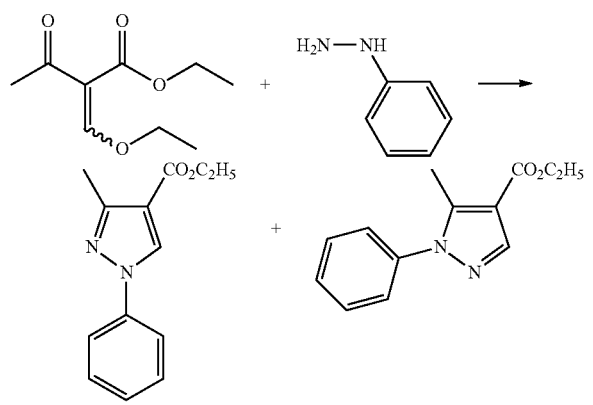

A solution of ethyl 2-(ethoxymethylidene)-3-oxobutanoate (2.0 g) in 11 ml of ethanol are rapidly added dropwise to a solution of 1-phenylhydrazine (1.16 g) in 10 ml of ethanol, cooled to 0° C. The mixture is heated to room temperature and is left under stirring overnight.

At the end of the reaction, the mixture is cooled to 0° C. and 30.0 ml of HCl at 10% are added. The phases are separated and the aqueous phase is extracted twice with ethyl acetate. The joined organic phases are first washed with fresh water and then with brine. They are subsequently anhydrified with Na₂SO₄ and the solvent is evaporated at reduced pressure.

2.46 g or raw product are obtained, in the form of an oil, containing a 6:94 mixture of ethyl 1-phenyl-3-methyl-1H-pyrazole-4-carboxylate and ethyl 1-methyl-5-phenyl-1H-pyrazolecarboxylate isomers.

The invention claimed is:
1. A process for the synthesis of pyrazoles of general formula (I)

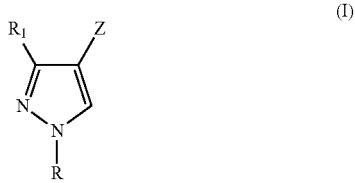

comprising the following steps:
i) a compound of general formula (II)

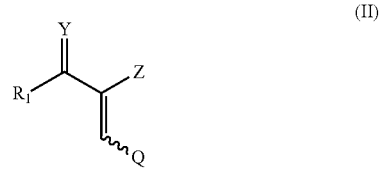

and a 1,2-di-substituted hydrazine of general formula (III)

are mixed to form a reaction intermediate having a general formula (IV)

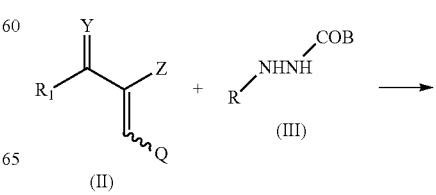

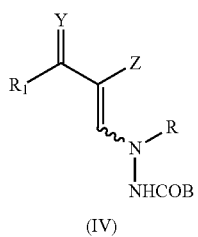

(IV)

ii) the reaction mixture obtained in step i), in acidic environment, cyclizes to form a pyrazole of general formula (I), according to the reaction scheme 1

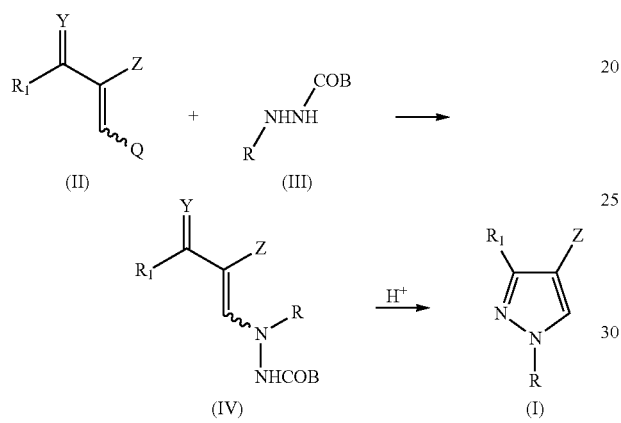

wherein in said formulas:

R represents a $C_1$-$C_6$ alkyl group or a $C_1$-$C_6$ haloalkyl group, said groups being optionally substituted with one or more groups selected from R', OR', $S(O)_nR'$; or R represents a $C_3$-$C_6$ cycloalkyl group, a $C_4$-$C_9$, cycloalkylalkyl group, a $C_2$-$C_6$ alkenyl group, a $C_2$-$C_6$, alkinyl group, a $C_6$-$C_{10}$ aryl group, a $C_7$-$C_{12}$ arylalkyl group, a 5 or 6 atoms heterocyclic ring containing from 1 to 3 heteroatoms selected from N, O, S, all these groups being optionally substituted by one or more groups selected from halogen atoms, R', OR', NR'R", $S(O)_mR'$, CONR'R", COR', $CO_2R'$, CN, $NO_2$;

$R_1$ represents a $C_1$-$C_6$ alkyl group or a $C_1$-$C_6$ haloalkyl group, said groups being optionally substituted with one or more groups selected from R', OR', $S(O)_nR'$; or $R_1$ represents a $C_3$-$C_6$ cycloalkyl group, a $C_4$-$C_9$, cycloalkylalkyl group, a $C_6$-$C_{10}$ aryl group, a $C_7$-$C_{12}$ arylalkyl group, all these groups being optionally substituted by one or more groups selected from halogen atoms, R', OR', $S(O)_mR'$, NR'R", CONR'R", COR', $CO_2R'$, $NO_2$, CN;

Z represents a $CO_2R_2$ group, a $CONR_3R_4$ group or a CN group;

$R_2$ represents a $C_1$-$C_6$ alkyl group, a $C_1$-$C_6$ haloalkyl group, said groups being optionally substituted with one or more groups selected from R', OR', SR'; or $R_2$ represents a $C_3$-$C_6$ cycloalkyl group, a $C_4$-$C_9$, cycloalkylalkyl group, a $C_6$-$C_{10}$ aryl group, a $C_7$-$C_{12}$ arylalkyl group, all these groups being optionally substituted by one or more groups selected from halogen atoms, R', OR', $S(O)_mR'$, NR'R", CONR'R", COR', $CO_2R'$;

$R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, a $C_3$-$C_6$ cycloalkyl group, a $C_4$-$C_9$, cycloalkylalkyl group, a $C_2$-$C_6$ alkenyl group, a $C_2$-$C_6$, alkinyl group, a 5 or 6 atoms heterocyclic ring, containing from 1 to 3 heteroatoms selected from N, O, S, all these groups being optionally substituted by one or more groups selected from halogen atoms, R', OR', NR'R", $S(O)_mR'$, CONR'R", COR', $CO_2R'$, CN, $NO_2$; or $R_3$ and $R_4$, together with the nitrogen atom to which they are bound, represent a 5 or 6 atoms heterocyclic nitrogen ring;

Y represents an oxygen or sulphur atom;

Q represents an $OR_5$, a $SR_5$, a $NR_6R_7$ group;

$R_5$ represents a $C_1$-$C_6$ alkyl group, optionally substituted with one or more groups selected from halogen atoms, R', OR', SR'; or $R_5$ represents a $C_3$-$C_6$ cycloalkyl group, a $C_6$-$C_{10}$ aryl group, a $C_7$-$C_{12}$ arylalkyl group, all these groups being optionally substituted by one or more groups selected from halogen atoms, R', OR', $S(O)_mR'$, NR'R", CONR'R", COR', $CO_2R$;

$R_6$ and $R_7$, equal to or different from each other, represent a hydrogen atom, a $C_1$-$C_6$ alkyl group, a $C_6$-$C_{10}$ aryl group, a $C_7$-$C_{12}$ arylalkyl group; or $R_6$ and $R_7$, together with the nitrogen atom to which they are bound, represent a 5 or 6 atoms heterocyclic nitrogen ring;

B represents a $R_8$, $OR_9$ or $NR_{10}R_{11}$ group;

$R_8$ and $R_9$ represent a $C_1$-$C_6$ alkyl group, a $C_2$-$C_6$ alkenyl group, a $C_3$-$C_6$ cycloalkyl group, a $C_6$-$C_{10}$ aryl group, a $C_7$-$C_{12}$ arylalkyl group, a 5 or 6 atoms heterocyclic ring, containing from 1 to 3 heteroatoms selected from N, O, S, all these groups being optionally substituted by one or more groups selected from halogen atoms, R', OR', NR'R", $S(O)_mR'$, CONR'R", COR', $CO_2R'$, CN;

$R_{10}$ and $R_{11}$, equal to or different from each other, represent a hydrogen atom, a $C_1$-$C_6$ alkyl group, a $C_6$-$C_{10}$ aryl group, a $C_7$-$C_{12}$ arylalkyl group, all said groups being optionally substituted with one or more halogen atoms; or $R_{10}$ and $R_{11}$, together with the nitrogen atom to which they are bound, represent a 5 or 6 atoms heterocyclic nitrogen ring;

R' and R" represent a hydrogen atom, a $C_1$-$C_4$ alkyl group, a $C_1$-$C_4$ haloalkyl group;

m represents 0, 1 or 2.

2. Process according to claim 1, wherein step i) is carried out at a temperature comprised in the range of from −20° C. to the boiling temperature of the reaction mixture, preferably from −10° C. to 80° C. and step ii) is carried out at a temperature comprised in the range of from −10° C. to the boiling temperature of the reaction mixture, preferably from 0° C. to 40° C.

3. Process according to claim 1, wherein the acidic environment is obtained by addition of an inorganic or organic acid in step ii) or by using a compound of general formula (III) salified with an organic or inorganic acid.

4. Process according to claim 1, wherein in step ii) the organic or inorganic acid is present in a molar ratio ranging of from 0.01 to 10, preferably from 0.05 to 5, more preferably from 0.1 to 1.5, with respect to the compound of formula (III).

5. Process according to claim 3, wherein the organic or inorganic is a strong acid.

6. Process according to claim 5, wherein the inorganic acid is a strong acid selected from HCl, HBr, $H_2SO_4$.

7. Process according to claim 5, wherein the organic acid is a strong acid selected from $CF_3CO_2H$, $CH_3SO_3H$, $CF_3SO_3H$, p-toluensulphonic acid.

8. Process according to claim 1, wherein the compound of formula (II) and the compound of formula (III) are used in a molar ratio ranging of from 0.8 to 3, preferably from 0.8 to 1.5, more preferably they are used in equimolar amounts.

9. Process according to claim 1, wherein the process is carried out in presence of one or more organic solvent selected from aliphatic or cycloaliphatic hydrocarbons, chlorinated hydrocarbons, aromatic hydrocarbons, ethers, alcohols, glycols, ketones, nitriles, dipolar aprotic solvents.

10. Process according to claim 9, wherein the organic solvent is selected from toluene, xylene, methylene chloride, dichloroethane, methanol, ethanol, iso-propanol, tetrahydrofuran, dimethylformamide.

11. Process according to claim 1, for the preparation of pyrazoles of general formula (I)

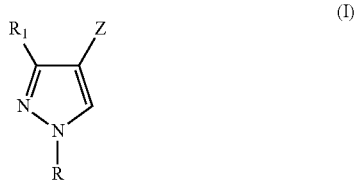

(I)

wherein:
R represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxy groups, $C_1$-$C_4$ haloalkoxy groups;
$R_1$ represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxy groups, $C_1$-$C_4$ haloalkoxy groups;
Z represents a $CO_2R_2$ group, a $CONR_3R_4$ group;
$R_2$ represents a $C_1$-$C_6$ alkyl group or a $C_1$-$C_6$ haloalkyl group; or represents a $C_6$-$C_{10}$ aryl group, a $C_7$-$C_{12}$ arylalkyl group, these groups being optionally substituted by one or more groups selected from halogen atoms, R', OR';
$R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, each of these groups being optionally substituted by one or more groups selected from halogen atoms, R', OR'; or $R_3$ and $R_4$, together with the nitrogen atom to which they are bound, represent a 5 or 6 atoms heterocyclic nitrogen ring;
R' and R" represent a hydrogen atom, a $C_1$-$C_4$ alkyl group, a $C_1$-$C_4$ haloalkyl group.

12. Process according to claim 11, wherein:
R represents a $C_1$-$C_6$ alkyl group or a phenyl optionally substituted with halogen atoms;
$R_1$ represents a methyl, a difluoromethyl, a trifluoromethyl or a phenyl optionally substituted with halogen atoms;
Z represents a $CO_2R_2$ group wherein $R_2$ represents a $C_1$-$C_6$ alkyl or haloalkyl group.

13. Process according to claim 11 or 12, wherein:
R represents a methyl group;
$R_1$ represents a methyl, a difluoromethyl, a trifluoromethyl;
Z represents a $CO_2R_2$ group wherein $R_2$ represents a $C_1$-$C_6$ alkyl or haloalkyl group.

14. Intermediate compounds of general formula (IV)

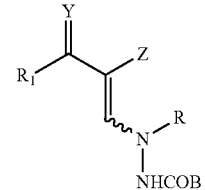

(IV)

wherein:
R represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxy groups, $C_1$-$C_4$ haloalkoxy groups;
$R_1$ represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxy groups, $C_1$-$C_4$ haloalkoxy groups;
Z represents a $CO_2R_2$ group, a $CONR_3R_4$ group;
$R_2$ represents a $C_1$-$C_6$ alkyl group or a $C_1$-$C_6$ haloalkyl group; or represents a $C_6$-$C_{10}$ aryl group, a $C_7$-$C_{12}$ arylalkyl group, these groups being optionally substituted by one or more groups selected from halogen atoms, R', OR';
$R_3$ and $R_4$, equal to or different from each other, represent a hydrogen atom, a $C_1$-$C_6$ alkyl group, a $C_6$-$C_{10}$ aryl group, a $C_7$-$C_{12}$ arylalkyl group, each of these groups being optionally substituted by one or more groups selected from halogen atoms, R', OR'; or $R_3$ and $R_4$, together with the nitrogen atom to which they are bound, represent a 5 or 6 atoms heterocyclic nitrogen ring;
R' and R" represent a hydrogen atom, a $C_1$-$C_4$ alkyl group, a $C_1$-$C_4$ haloalkyl group;
Y represents an oxygen atom;
B represents a $R_8$, $OR_9$ or $NR_{10}R_{11}$ group;
$R_8$ represents a $C_1$-$C_6$ alkyl group optionally substituted with halogen atoms, or a $C_6$-$C_{10}$ aryl group;
$R_9$ represents a $C_1$-$C_6$ alkyl group optionally substituted with halogen atoms, or a $C_6$-$C_{10}$ aryl group;
$R_{10}$ and $R_{11}$, equal to or different from each other, represent a hydrogen atom, a $C_1$-$C_6$ alkyl group, a $C_6$-$C_{10}$ aryl group.

15. Intermediate compounds of general formula (IV) according to claim 14, wherein:
R represents a methyl group;
$R_1$ represents a methyl, a difluoromethyl or a trifluoromethyl group;
Z represents a $CO_2R_2$ group, wherein $R_2$ represents a $C_1$-$C_6$ alkyl or haloalkyl group;
B represents a $R_8$, $OR_9$ or $NR_{10}R_{11}$ group;
$R_8$ represents a $C_1$-$C_6$ alkyl group optionally substituted with halogen atoms, or a $C_6$-$C_{10}$ aryl group;
$R_9$ represents a $C_1$-$C_6$ alkyl group optionally substituted with halogen atoms, or a $C_6$-$C_{10}$ aryl group;
$R_{10}$ and $R_{11}$, equal to or different from each other, represent a hydrogen atom, a $C_1$-$C_6$ alkyl group, a $C_6$-$C_{10}$ aryl group.

* * * * *